United States Patent
Thomas

(10) Patent No.: US 9,025,145 B2
(45) Date of Patent: May 5, 2015

(54) FLOW CYTOMETRY SYSTEM AND METHOD FOR APPLYING GAIN TO FLOW CYTOMETRY DATA

(75) Inventor: Michael Adeeb Thomas, Davie, FL (US)

(73) Assignee: Beckman Coulter Biomedical, LLC, Washington, DC (US)

( * ) Notice: Subject to any disclaimer, the term of this patent is extended or adjusted under 35 U.S.C. 154(b) by 114 days.

(21) Appl. No.: 13/138,560

(22) PCT Filed: Mar. 2, 2010

(86) PCT No.: PCT/US2010/000626
§ 371 (c)(1),
(2), (4) Date: Sep. 28, 2011

(87) PCT Pub. No.: WO2010/101623
PCT Pub. Date: Sep. 10, 2010

(65) Prior Publication Data
US 2012/0019825 A1    Jan. 26, 2012

Related U.S. Application Data

(60) Provisional application No. 61/209,042, filed on Mar. 2, 2009.

(51) Int. Cl.
*G01N 21/00* (2006.01)
*G01N 15/14* (2006.01)
*G01N 21/31* (2006.01)
*G01N 21/85* (2006.01)

(52) U.S. Cl.
CPC ............ *G01N 15/1429* (2013.01); *G01N 21/31* (2013.01); *G01N 21/8507* (2013.01); *G01N 15/1459* (2013.01); *G01N 2015/1486* (2013.01); *G01N 2015/149* (2013.01)

(58) Field of Classification Search
CPC .... G01N 21/8507; G01N 21/31; G01N 21/59
USPC ......................................... 356/338, 343, 337
See application file for complete search history.

(56) References Cited

U.S. PATENT DOCUMENTS

| | | | |
|---|---|---|---|
| 5,411,029 A | 5/1995 | Hirai | |
| 5,540,494 A * | 7/1996 | Purvis et al. | 356/73 |
| 6,573,991 B1 * | 6/2003 | Debreczeny et al. | 356/336 |
| 7,471,393 B2 * | 12/2008 | Trainer | 356/336 |
| 2005/0151968 A1 * | 7/2005 | Drake et al. | 356/338 |

(Continued)

OTHER PUBLICATIONS

PCT Search Report for Serial No. WO 2010/101623 dated Apr. 20, 2010.

(Continued)

*Primary Examiner* — Tarifur Chowdhury
*Assistant Examiner* — Isiaka Akanbi
(74) *Attorney, Agent, or Firm* — Merchant & Gould, P.C.

(57) ABSTRACT

The invention relates to a flow cytometer system and method to apply a gain to data measurements to improve the display of the data measurements. The method for applying a gain to data detected in a flow cytometer, involves obtaining measurements from a detector in a flow cytometer, applying a gain to the measurements to produce shifted measurements to allow for improved display of the shifted measurements while maintaining the relationship between data points of the shifted measurements and displaying the shifted measurements on a display.

5 Claims, 16 Drawing Sheets

(56) References Cited

U.S. PATENT DOCUMENTS

| | | |
|---|---|---|
| 2008/0010019 A1 | 1/2008 | Thomas |
| 2008/0215297 A1 | 9/2008 | Goebel et al. |
| 2008/0221711 A1* | 9/2008 | Trainer .......................... 700/54 |
| 2008/0319680 A1* | 12/2008 | Fox et al. ....................... 702/21 |

OTHER PUBLICATIONS

Accuri Cytometers; CFlow User Guide, 2009, 71 pages.

* cited by examiner

FLOW CYTOMETRY SYSTEM AND METHOD FOR APPLYING GAIN TO FLOW CYTOMETRY DATA

CROSS-REFERENCE TO RELATED APPLICATIONS

This Application is a U.S. National Stage of PCT International patent application No. PCT/US2010/000626, filed Sep. 28, 2011, which claims the benefit of U.S. Provisional Application No. 61/209,042, filed Mar. 2, 2009. This application is also related to U.S. patent application Ser. No. 11/544,239 (2007/0085997) and U.S. patent application Ser. No. 11/825,523 (2008/0010019), the entire contents of which are incorporated herein by reference.

TECHNICAL FIELD

The present invention relates to a flow cytometry system and method for applying a gain to flow cytometry data. More particularly, the system and method that applies a gain to one or more flow cytometry data ranges without the need for adjusting flow cytometer instrument hardware settings.

BACKGROUND OF THE INVENTION

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light, usually laser light, of a single frequency (color) is directed onto a hydrodynamically focused stream of fluid. A number of detectors are aimed at the point where the stream passes through the light beam; one in line with the light beam (Forward Scatter or FSC) and several perpendicular to it (Side Scatter or SSC) and one or more fluorescent detectors. Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness.

Flow cytometry systems or flow cytometers convert light signals from a cell sample or particle to electronic pulses and then an analog-to-digital converter (ADC) coverts the electronic pulses to channel numbers. The channel numbers represent flow cytometry data which can be presented on a display, such as a computer screen or printer, with the maximum acquired channel being presented at the end of the display object. As the technology for acquisition modules improves, cytometers are collecting wider dynamic data channel ranges. For example, instead of collecting four decades of dynamic data range, cytometers can now collect six decades of dynamic data range. Under this broader data range, data previously viewed in channels for three or four decades of dynamic data range are now viewed in six decades of dynamic data range.

Known flow cytometry systems present data on displays with the maximum acquired channel being presented at the end of the display object. For example older cytometers that only collected data from channel ranges 0 to 1023, would display the data on the display object from channels 0 to 1023. Newer cytometers, which collect broader data ranges (e.g., example 0 to 262,144), adjust the end of the display to 262,144 to accommodate the broader data ranges collected. In other words, prior art flow cytometer systems present the collected flow cytometry data with a fixed scale, and adjusts the flow cytometer hardware settings such as hardware gain, light source intensity, or PMT voltage in order to move particles with varying intensities to different locations in the fixed display area. A disadvantage of these systems is that in order to present the flow cytometry data at a desired location in the fixed area display, the cell sample must be rerun through the flow cytometer, at the adjusted hardware settings. These systems may be imprecise and the cell sample may have to be rerun several times before finding the desired settings of gain, intensity or voltage. In addition, old cell samples are not always available to be rerun and valuable data can be lost.

Because current flow cytometry systems fix the end of the channel range to the end of the display, in order to view cell samples having particles with varying intensities in a different location in the fixed display area, adjustments must be made to the flow cytometer hardware settings (e.g., hardware gain, light source intensity, and PMT voltage) and the cell sample must be rerun through the flow cytometer.

Thus, there exists a need for a more efficient cytometry system which can present cytometry data in alternate locations on the fixed area display object without the need to adjust cytometer instrument hardware settings and rerun the cell sample through the flow cytometer. The present invention satisfies this need and provides related advantages as well.

The present system and method, described herein, allows for a fixed hardware setting for all the possible range of particle sizes and intensities. Instead of adjusting the hardware settings, a mathematical operator or software gain is applied to the flow cytometry data. The data can then be presented in a different location on the display object other than the original fixed gain location.

SUMMARY OF THE INVENTION

The invention relates to flow cytometers and methods to apply a gain to flow cytometry data. The present invention provides a device for detecting and identifying sample particles in a fluid and applying a gain to acquired data. The device includes a photo detector configured to generate an output signal in response to light scattering of sample particles, an amplifier coupled to the detector for amplifying the output signal, an analog to digital converter coupled to the amplifier configured to convert the output signal into a digital output signal and a processor coupled to the analog to digital converter configured to receive the digital output signal and generate display information relating to the digital output signal, wherein the processor applies a gain to the display information to shift the values of the display information. The device may also include a display for presenting the display information to a user and a flow cell to align the sample particles to pass through a light beam.

The present invention also provides a flow cytometer system for analyzing the content of a sample and applying a gain to the acquired data. The system may contain a detector for measuring a data signal associated with a sample and a processing means for applying a pre-selected gain to the data signal. The processing means may apply a gain sufficient to shift the display of the data while maintaining the existing relationship between the data points of the data signal. The system may also include an analog to digital converter configured to convert the data signal into a digital data signal and a display.

Also, the method for applying a gain to data detected in a flow cytometer, described in more detail below, involves obtaining measurements from a detector in a flow cytometer, applying a gain to the measurements to produce shifted measurements to allow for improved display of the shifted measurements while maintaining the relationship between data points of the shifted measurements and displaying the shifted measurements on a display.

BRIEF DESCRIPTION OF THE DRAWINGS

To understand the present invention, it will now be described by way of example, with reference to the accompanying drawings in which.

DETAILED DESCRIPTION

Figure 1:
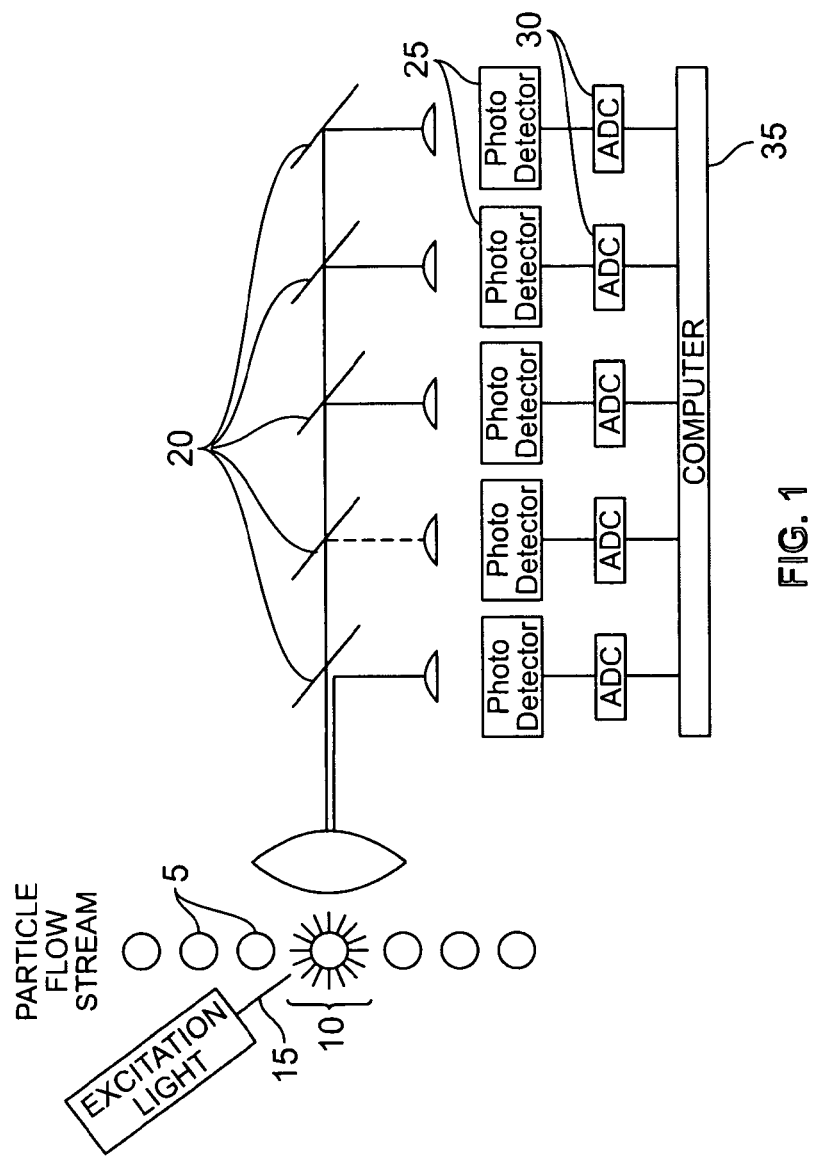
FIG. 1 is a schematic diagram of a flow cytometer showing a particle flowing through a sensing zone, where the particle is excited by a beam of light that then causes the particle to fluoresce and/or scatter light. The light is then separated by filters into portions of the electromagnetic (EM) spectrum and detected with photomultiplier tubes (PMT). The analog pulse is preprocessed and then digitized with an analog to digital converter (ADC). The data is then stored and analyzed by a computer system.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to the figures, a flow cytometry system and method is provided which can apply various gains to flow cytometry data and present the data as desired on a display device. The cytometry system includes various flow cytometer components, a processor with hardware and software, and a display device.

In the following description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form.

The present invention also includes various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software. While embodiments of the present invention will be described with reference to flow cytometers which collect four or six decades of dynamic range data, the system and method described herein are equally applicable to other types of cytometers as well.

As shown in FIG. 1, a flow cytometer is a device that flows a particle 5 through a sensing zone 10 where the particle is normally excited by a beam of light 15 from a light source 17, such as a laser. The light source 15 causes the particle 5 to fluoresce and/or scatter light. The particles 5 pass through the sensing zone 10 in approximately five microseconds. The fluoresced or scattered light is then separated by filters 20 into portions of the electromagnetic spectrum, usually about twenty nanometers wide, and detected with a photo detector, such as a Photomultiplier Tubes (PMT) 25. The analog pulse is then converted to a digital data stream using Analog to Digital Converters (ADCs) 30. The digital data stream is then processed for its various values by an analysis system 35 or computer. The analysis system 35 is able to generate or extract data relating to the data stream, for example the, signal peak, the signal width, the integral of the signal, or log value of the pulse. This data relates to characteristics of the particles 5. The analysis system 35 can also display the extracted measurement in a form that a user of the system can comprehend.

Flow cytometers have grown from single parameter instruments to instruments that may have multiple fluorescent parameters along with multiple light scatter and volume parameters. With the addition of each parameter, an additional detector and data conversion channel along with the necessary light separation filter system is added. As shown in the schematic diagram of FIG. 1, five detectors and corresponding data conversion channels are shown.

The flow cytometry system obtains and stores data generated from an exemplary flow cytometer. One example of a flow cytometry system with a flow cytometer that can be used to generate such data is the Cell Lab Quanta™ SC MPL by Beckman Coulter®. As shown schematically in FIG. 1, the primary systems of a flow cytometer are: (1) a flow cell—liquid stream (sheath fluid) carries and aligns the particles so that they pass in a single file through the light beam for sensing; (2) the optics, which gather and direct the light—commonly used are lamps (mercury, xenon); high power water-cooled lasers (argon, krypton, dye laser); low power air-cooled lasers (argon (488 nm), red-HeNe (633 nm), green-HeNe, HeCd (UV)); diode lasers (blue, green, red, violet); (3) photo detectors which receive the light; (4) electronics, such as the amplification system for amplifying and/or conditioning of signals and the Analog to Digital Conversion (ADC) system—which convert the signals from the detectors into digital data; and (5) the peripheral computer system for analysis and display of the signals. Note that although not shown, in FIG. 1, it is common for cytometry systems to include signal processing equipment between the ADC's and the computer to assist with the processing of data generated by the cytometer. For example, pulse processing equipment and/or a digital signal processors with micro-controllers could be used.

The present flow cytometer system may have applications in a number of fields, including but not limited to molecular biology, pathology, immunology, plant biology and marine biology. In the field of molecular biology it is especially useful when used with fluorescence tagged antibodies. These specific antibodies bind to antigens on the target cells and help to give information on specific characteristics of the cells being studied in the cytometer. It has broad application in medicine, especially in transplantation, hematology, tumor immunology and chemotherapy, and genetics. In marine biology, the autofluorescent properties of photosynthetic plankton can be exploited by flow cytometry in order to characterize abundance and community structure. In protein engineering, flow cytometry can be used in conjunction with yeast display and bacterial display to identify cell surface-displayed protein variants with desired properties.

When the cells or particles, as represented in an exemplary embodiment in FIG. 1, intercept the light source, they scatter light and if the particle is labeled with a fluorochrome, the fluorochromes are excited to a higher energy state and energy is released as a photon of light with specific spectral properties unique to that particular fluorochrome. The photon having specific spectral properties may also be used to determine various physical properties of the cells or particles. For example, forward scatter, or low-angle light scatter, is the amount of light that is scattered in the forward direction as laser light strikes the cell and is received by a detector. The magnitude of forward scatter is roughly proportional to the size of the cell, and this data can be used to quantify that parameter. Light scattering at larger angles, for example to the side, is caused by granularity and structural complexity inside the cell. This side-scattered light is focused through a lens system and is collected by a separate detector, usually located 90 degrees from the laser's path. Fluorescence data is collected in generally the same way as forward and side scatter data and can provide quantitative and qualitative data about fluorochrome-labeled cell surface receptors or intracellular molecules such as DNA and cytokines. In a population of labeled cells, some will be brighter than others. As each cell crosses the path of the laser, a fluorescence signal is generated. The fluorescent light is then directed to the appropriate detector.

Figure 2:
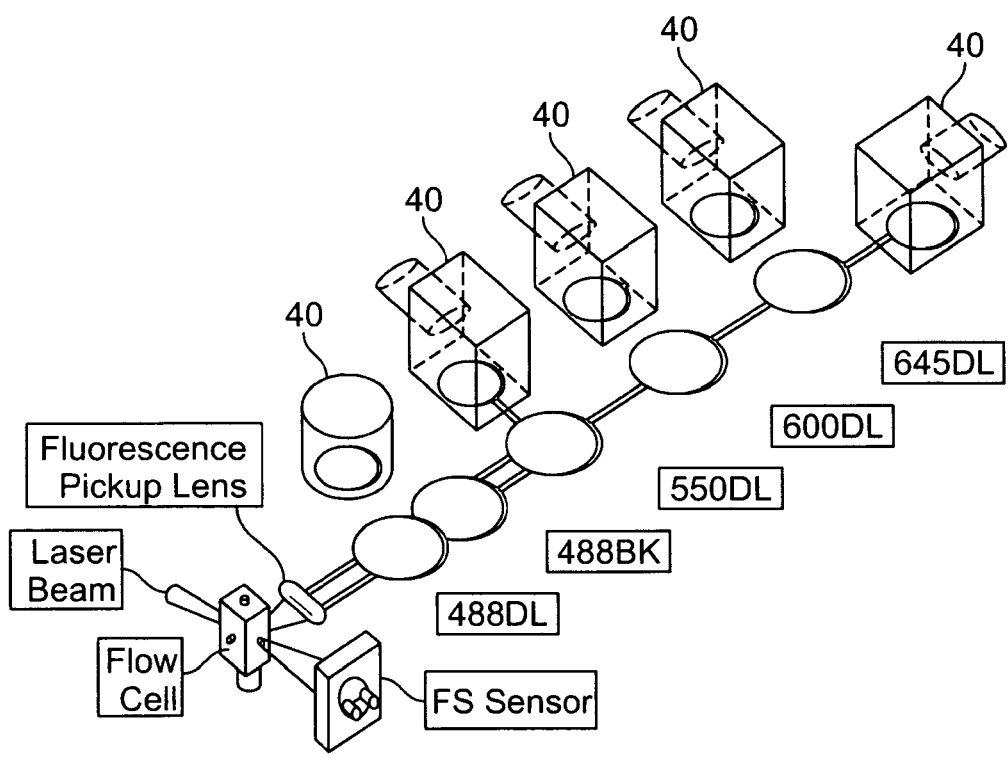
FIG. 2 is a schematic diagram of the optical components of an exemplary flow cytometer.

FIG. 2 shows a layout of the optical components of a flow cytometry system. As shown in FIG. 2, scattered and emitted light from cells and particles are converted to electrical pulses by optical detectors or sensors 40. Collimated (parallel light waveforms) light quanta is picked up by confocal lenses focused at the intersection point of cells and the light source. Light is sent to different detectors by using optical filters. For example, as shown, a 525 run band pass filter is placed in the light path prior to the detector FL1, and will only allow "green" light into the detector. The most common type of detector used in flow cytometry is the photomultiplier tube (PMT). When light hits a photodetector a small current (a few microamperes) is generated. Its associated voltage has an amplitude proportional to the total number of light photons received by the detector. Although exemplified herein with PMTs, it is understood that other detectors can be used, for example, a silicon photodiode detector.

The electrical pulses originating from light detected by the PMTs are then processed by a series of linear and log amplifiers. Logarithmic amplification may be used to measure fluorescence in cells. This type of amplification expands the scale for weak signals and compresses the scale for "strong" or specific fluorescence signals, resulting in a distribution that is easy to display on a histogram. After the different signals or pulses are amplified they are processed by an analog-to-digital converter (ADC) and converted to channel numbers. For example, the ADC assigns a channel number based on the pulse height for individual events. Therefore, brighter specific fluorescence events will yield a higher pulse height and thus a higher channel number when displayed. Although exemplified herein with ADCs it is understood that other methods can be used, including any suitable data collection element to collect the spectral information, for example, a device that samples and holds data and can then collect data in parallel.

Flow cytometry data output can be stored in the form of computer files using the flow cytometry standard (FCS) format, for example, FCS 2.0 or 3.0 standard. Data corresponding to one sample can be stored as a listmode file and/or a histogram file, which in turn allows for events to be plotted on a graphical scale (e.g., one parameter or two parameter histograms, and dot plots).

Figure 3:
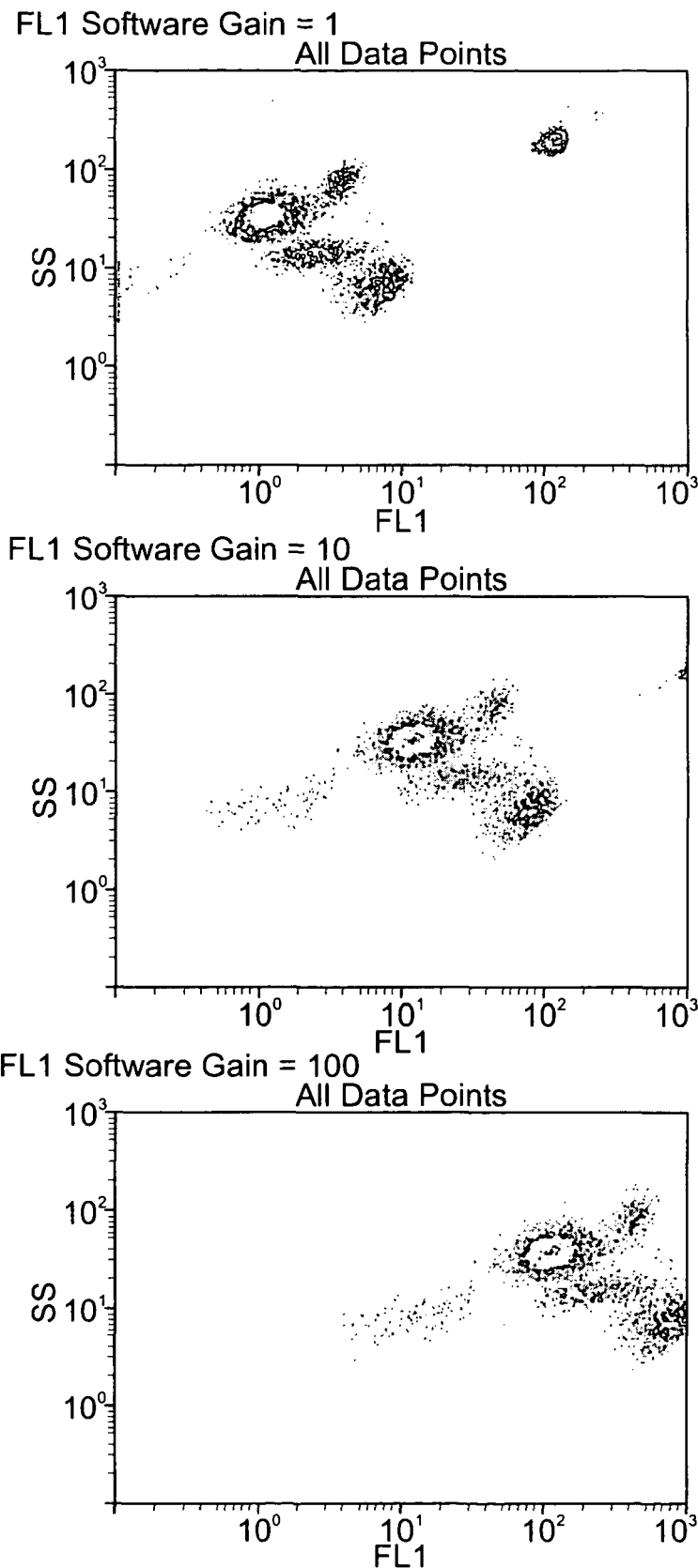
FIG. 3 shows three (3) dot plots which can be displayed from data collected with a single hardware setting, showing the data displayed with three different gain settings applied, using the cytometry system described herein.
Figure 4:
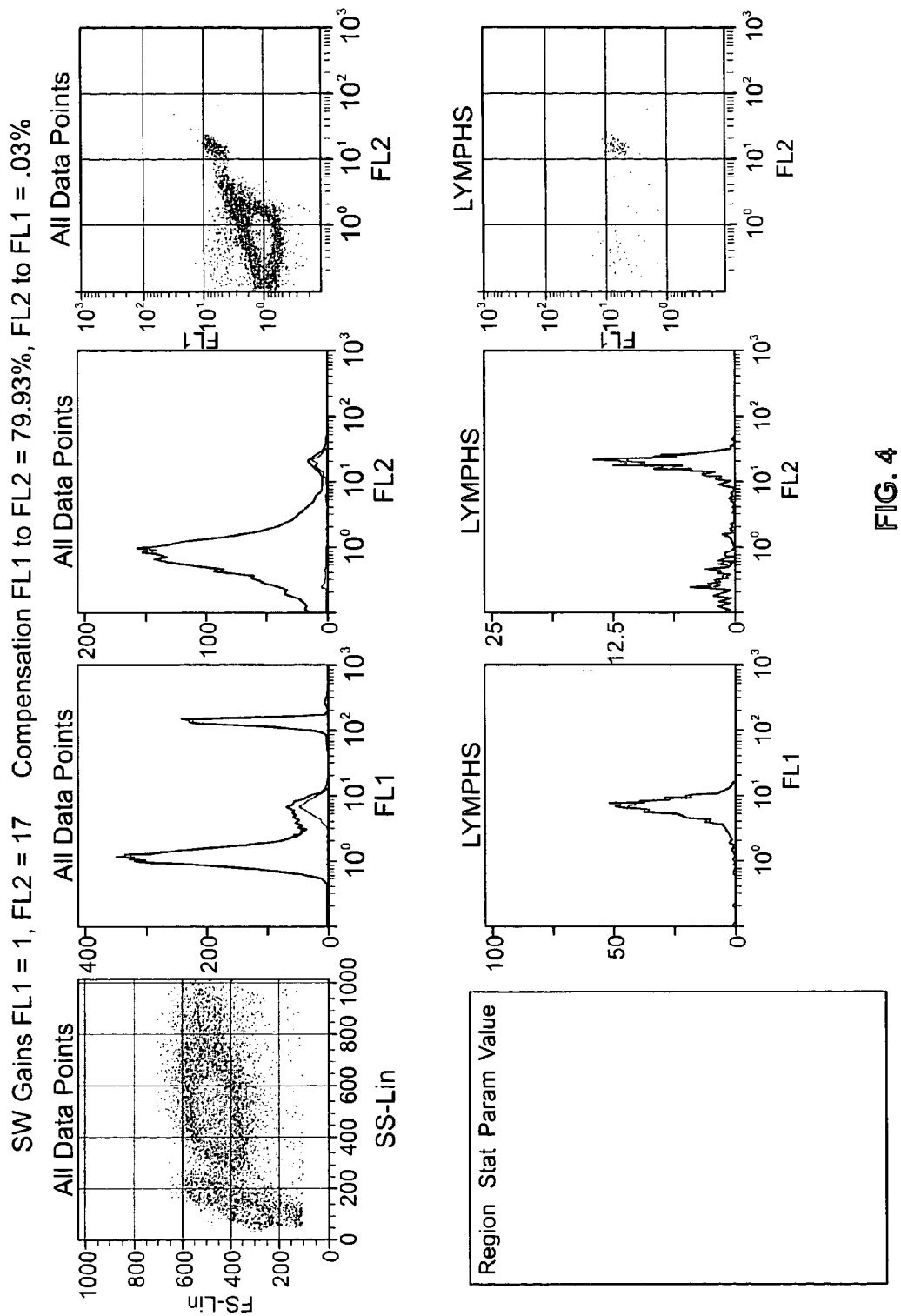
FIGS. 4-9 show several examples of dot plots and graphs of data points of a cell sample with two different fluorophores (FL1 and FL2) shown with varying gains applied to FL1 and with compensation values adjusted using the cytometry system described herein.
Figure 5:
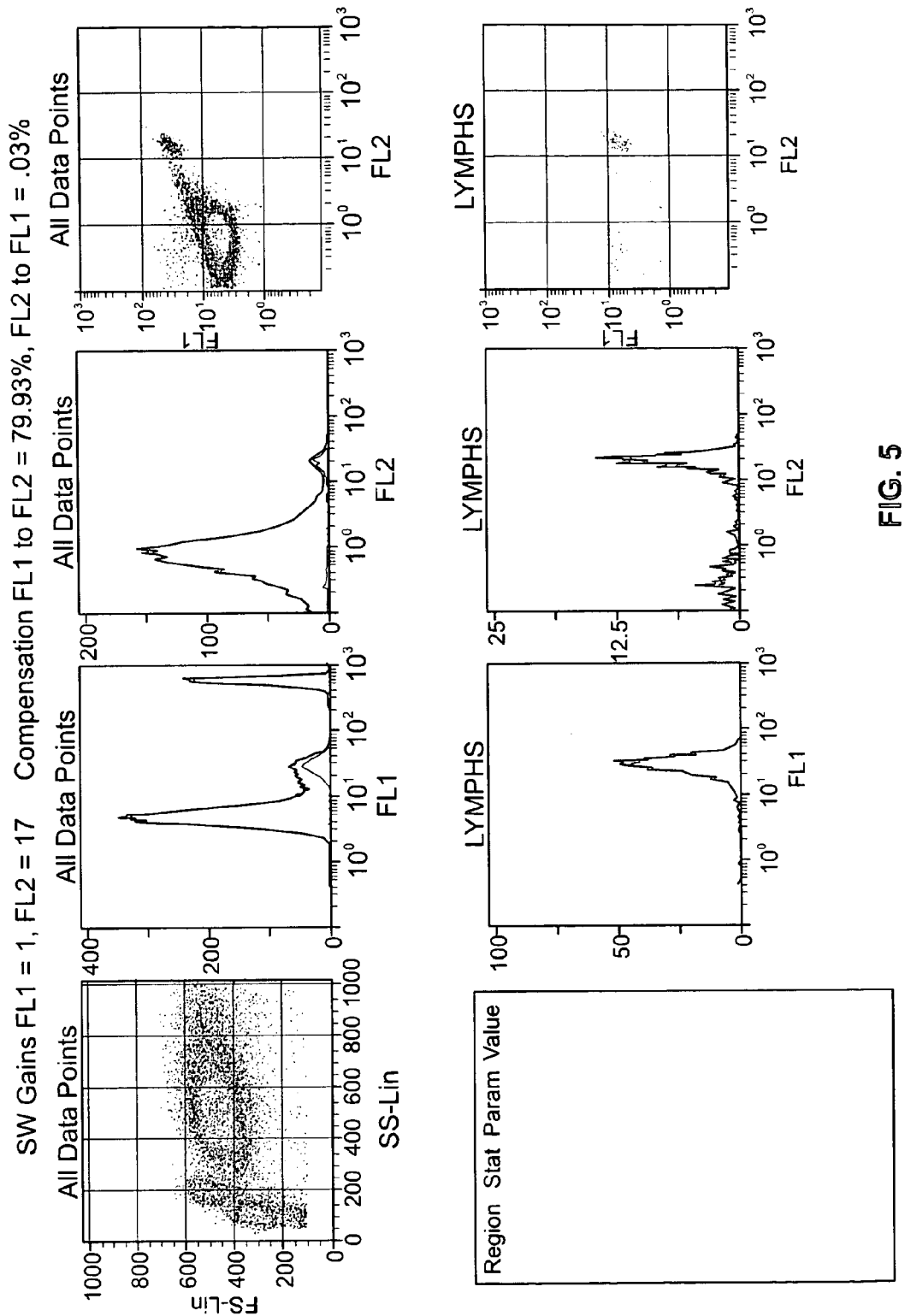
Figure 6:
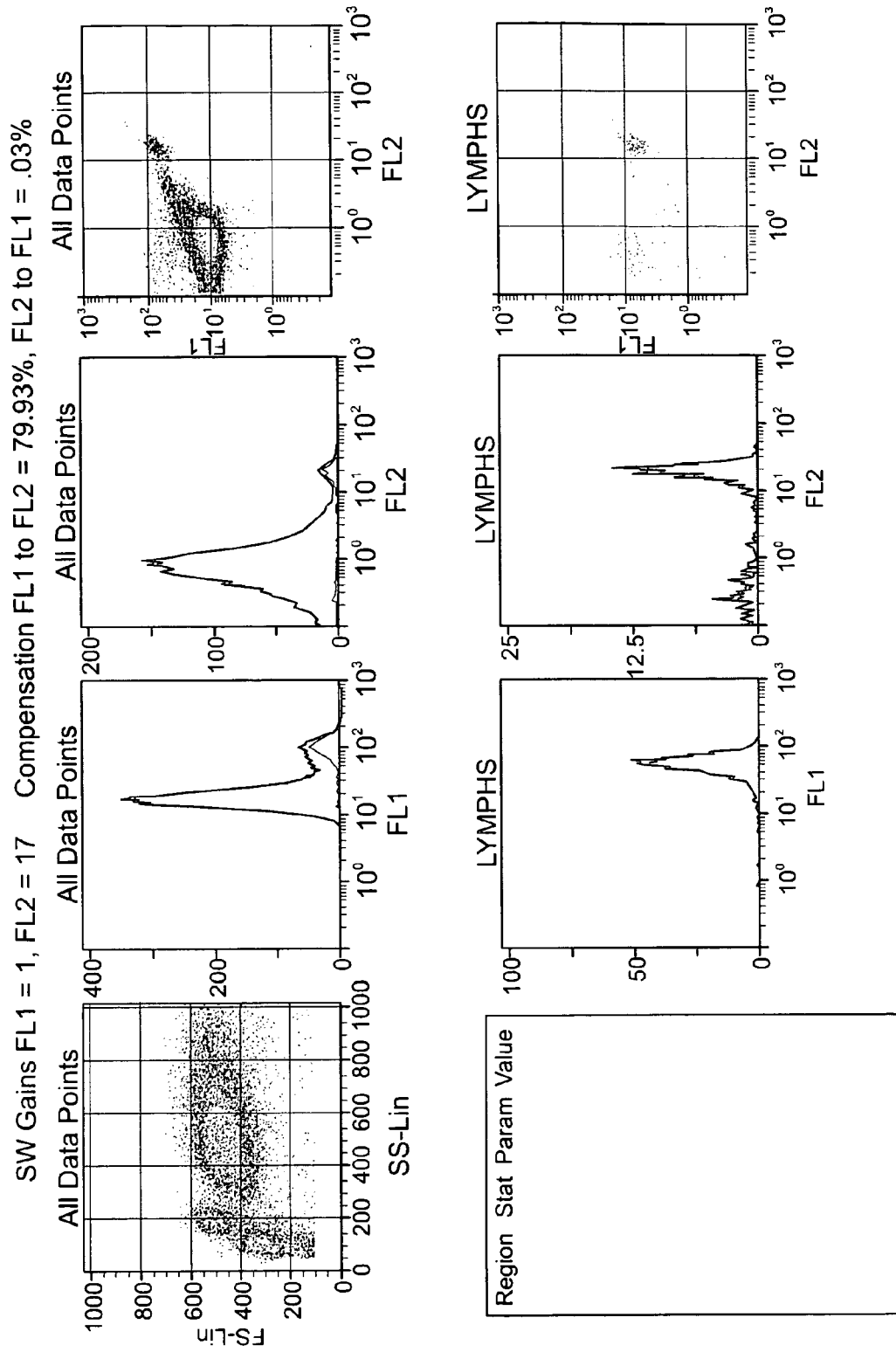
Figure 7:
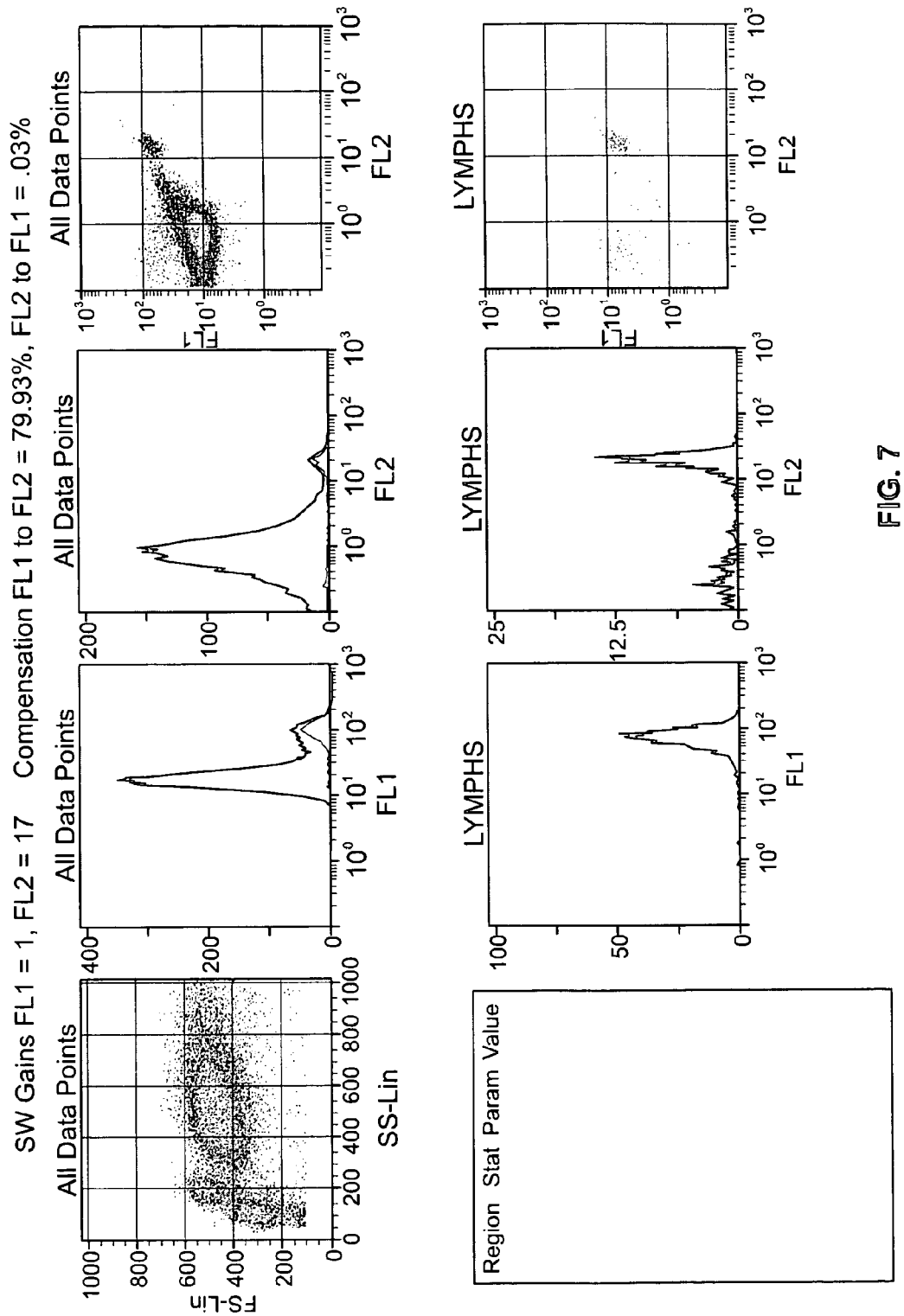
Figure 8:
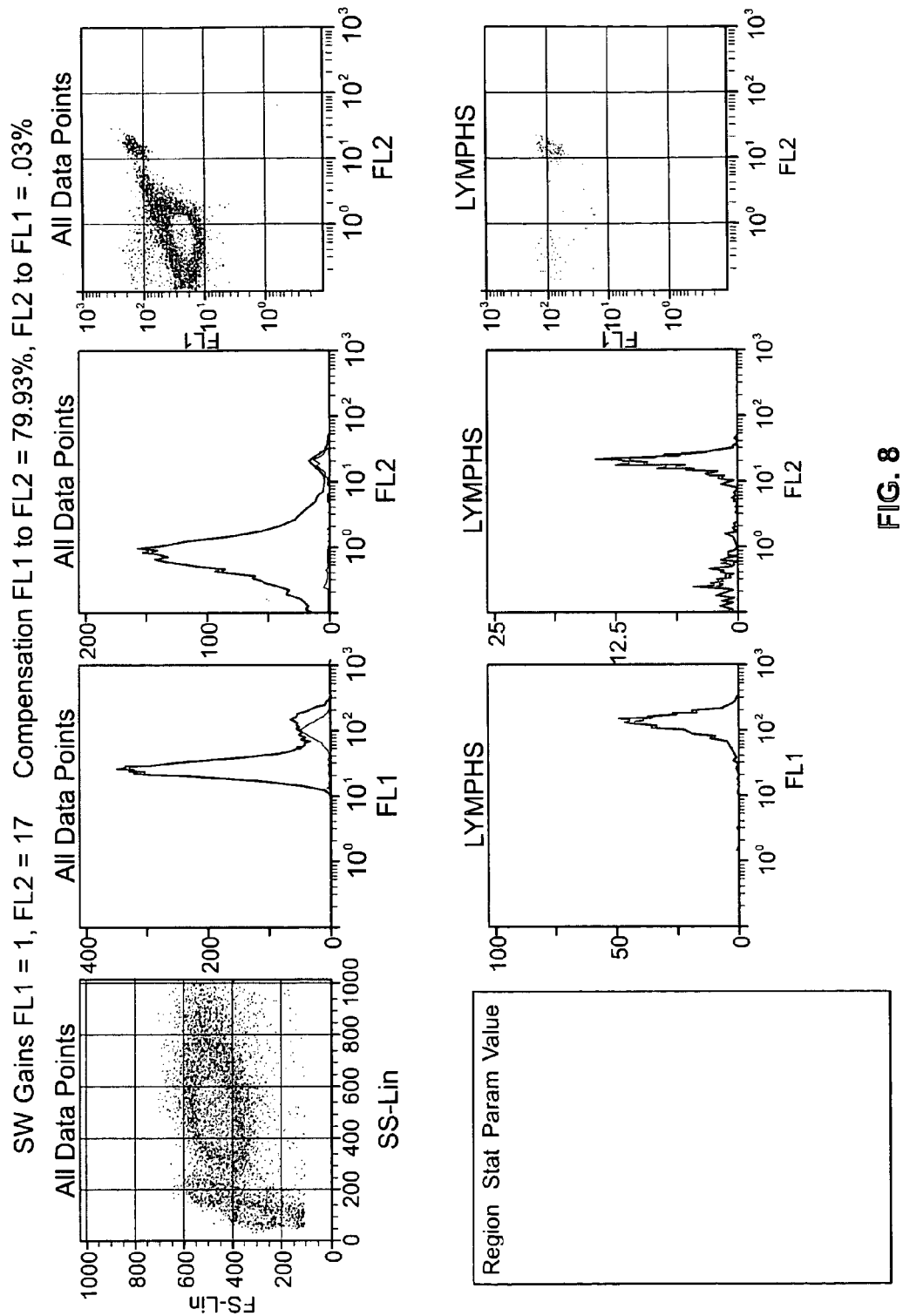
Figure 9:
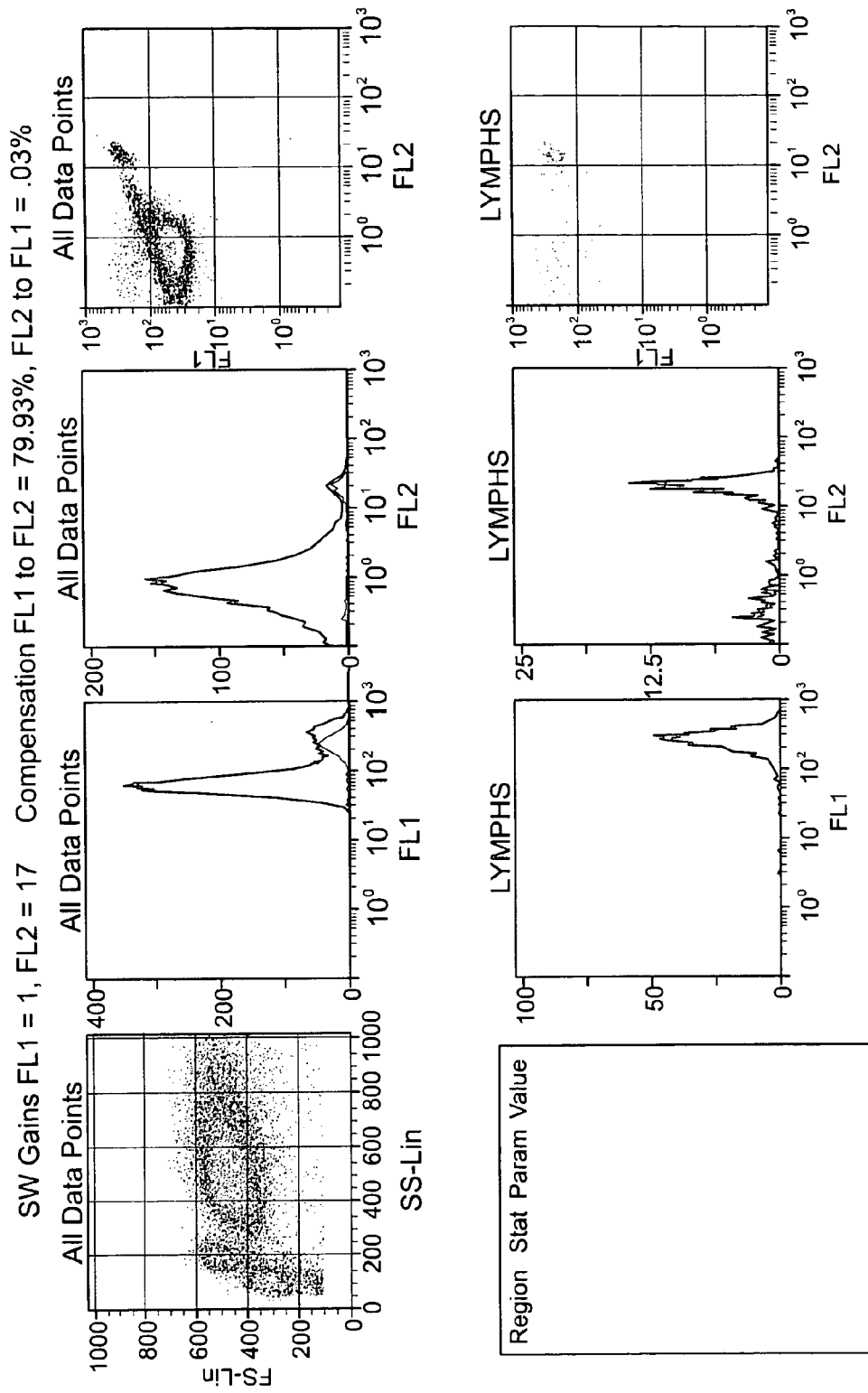
Figure 10:
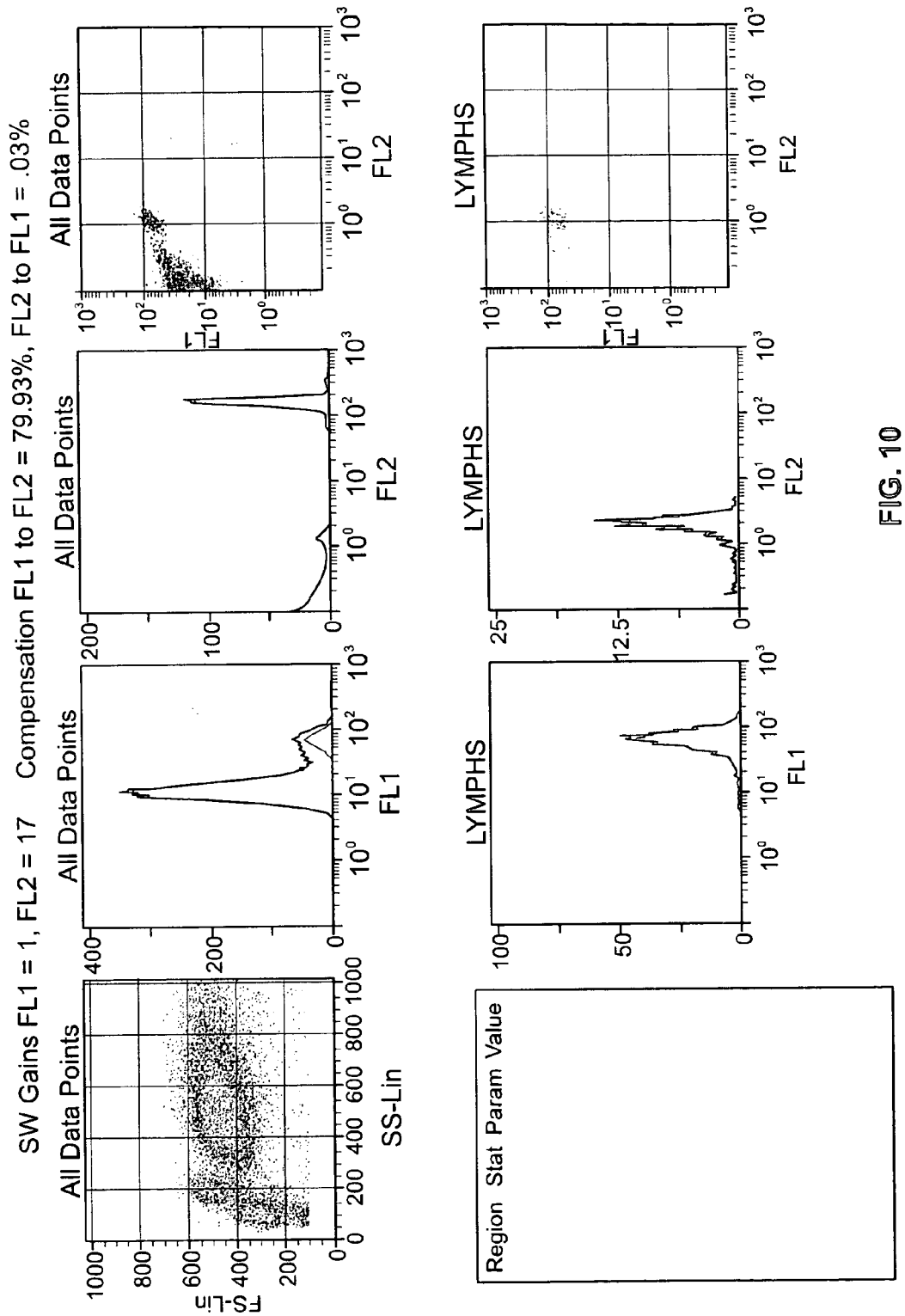
FIGS. 10-15 show several examples of dot plots and graphs of data points of a cell sample with two different fluorophores (FL1 and FL2) shown with varying software gains applied to FL2 and with compensation values adjusted using the cytometry system described herein.
Figure 11:
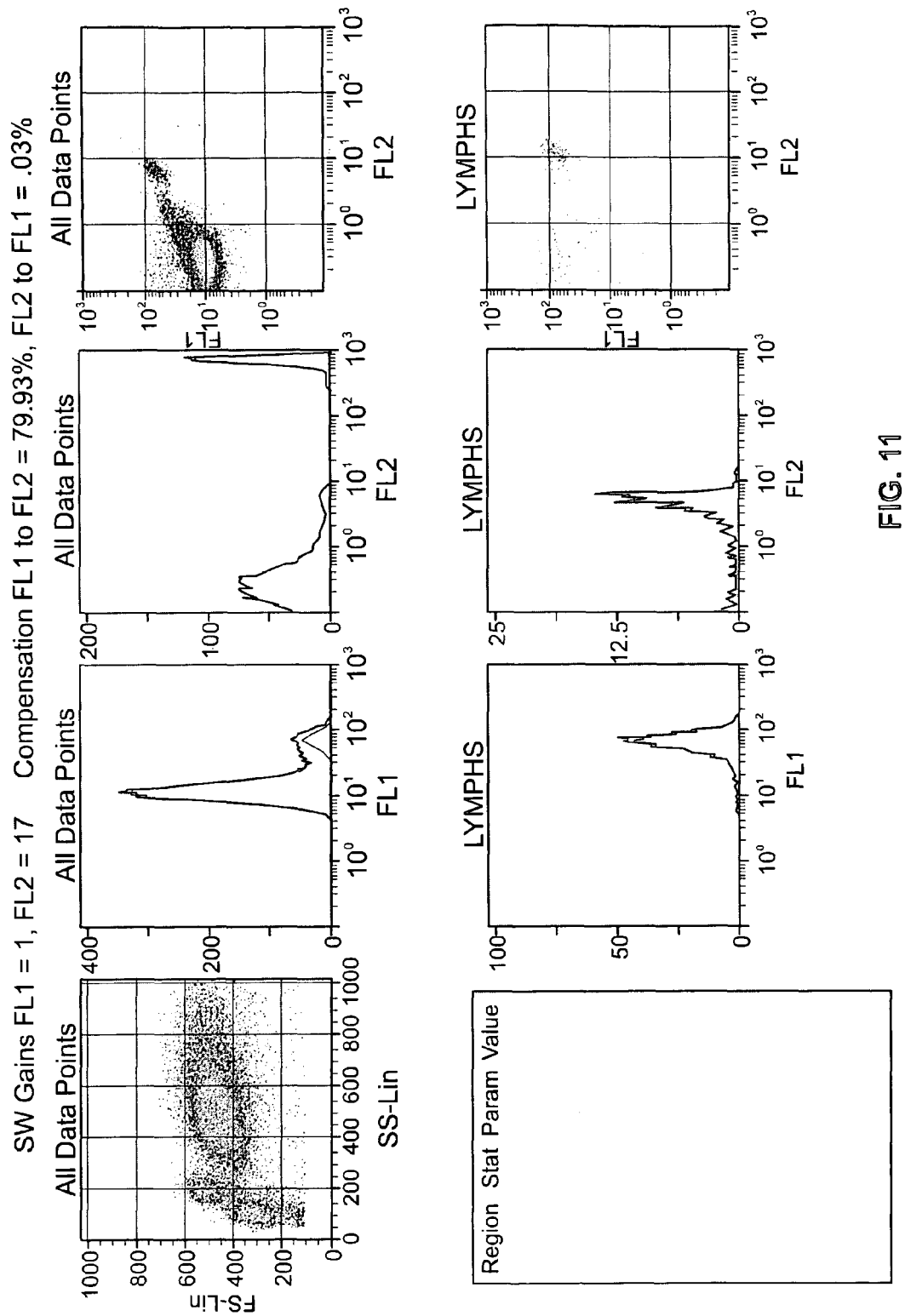
Figure 12:
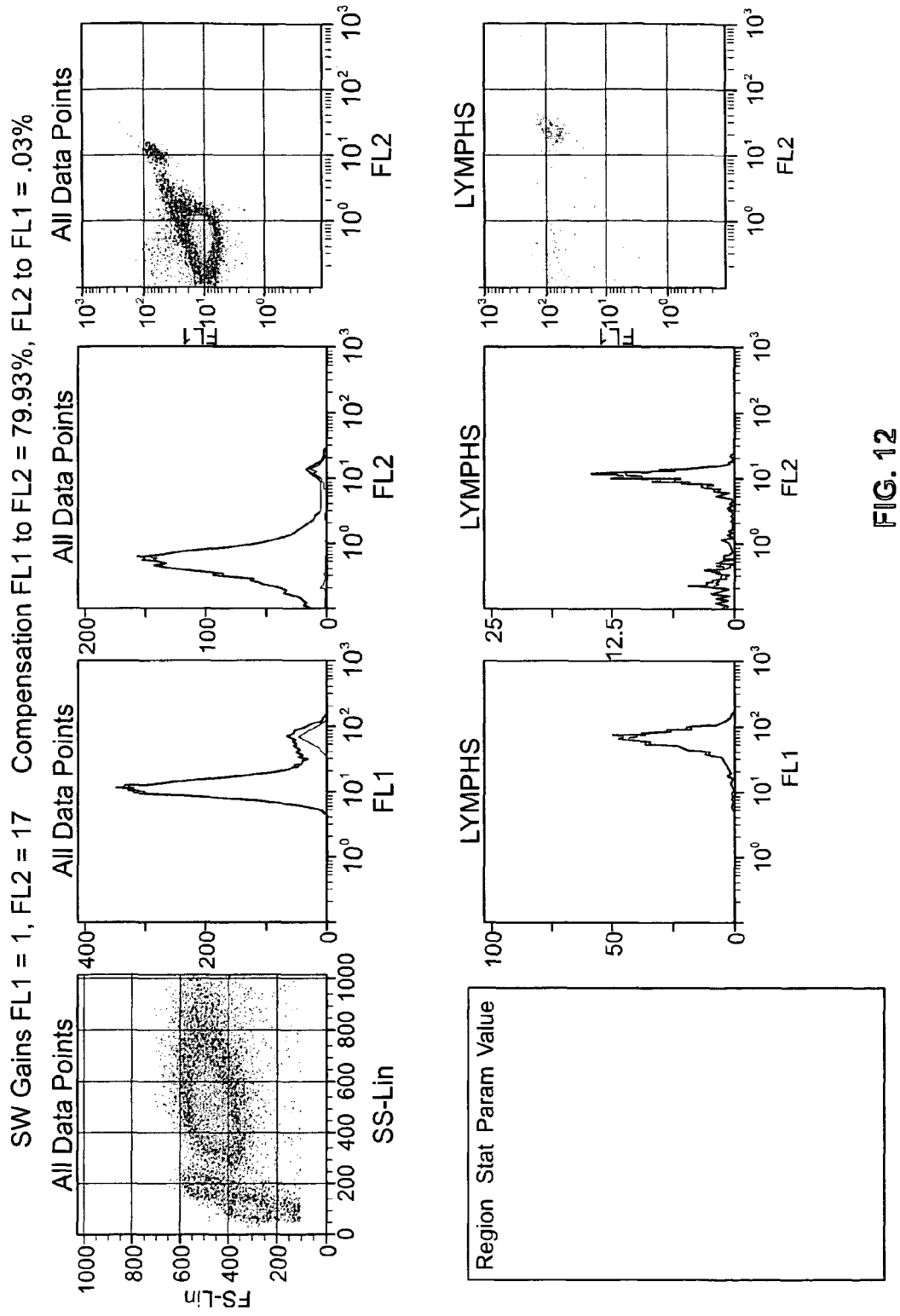
Figure 13:
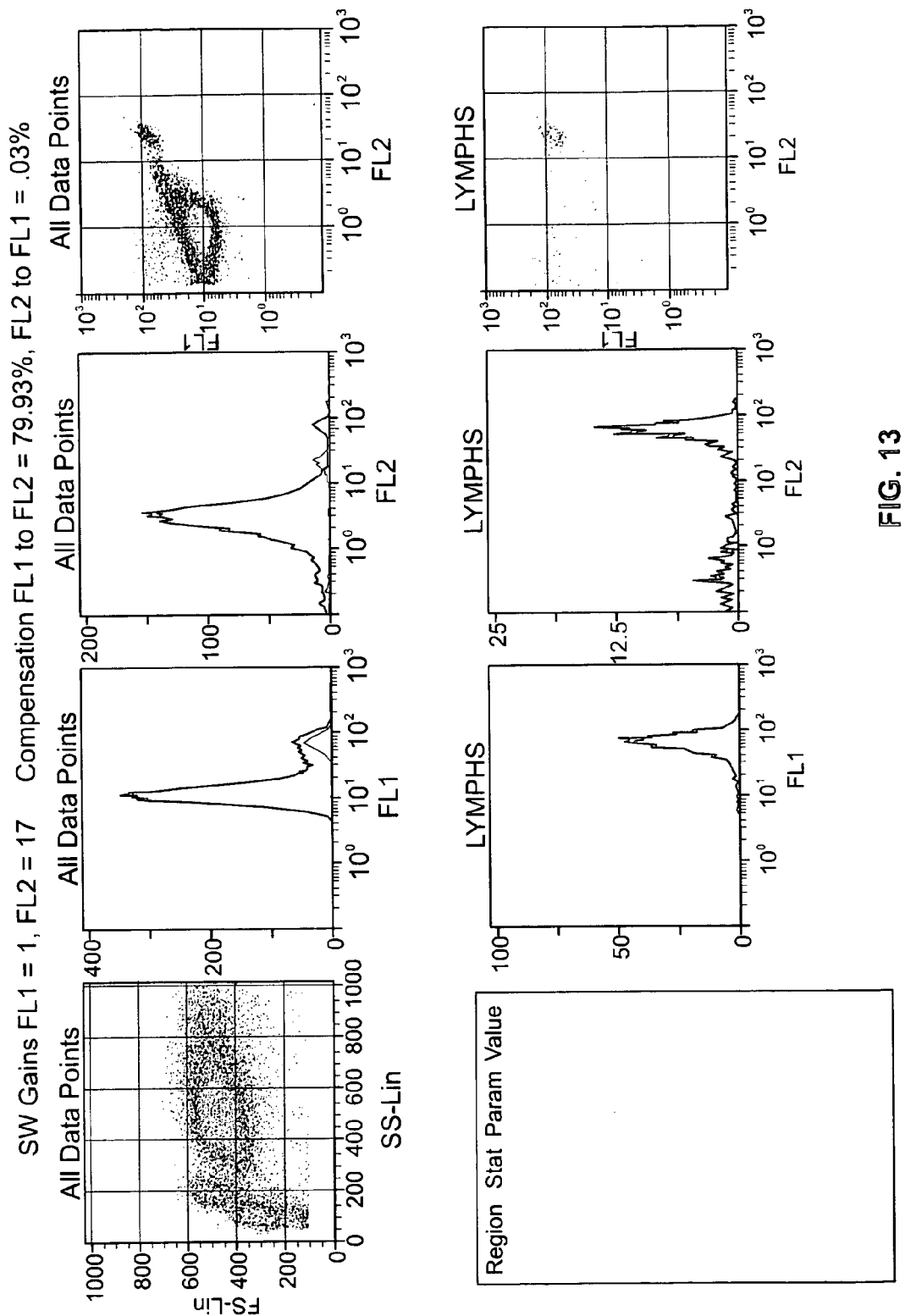
Figure 14:
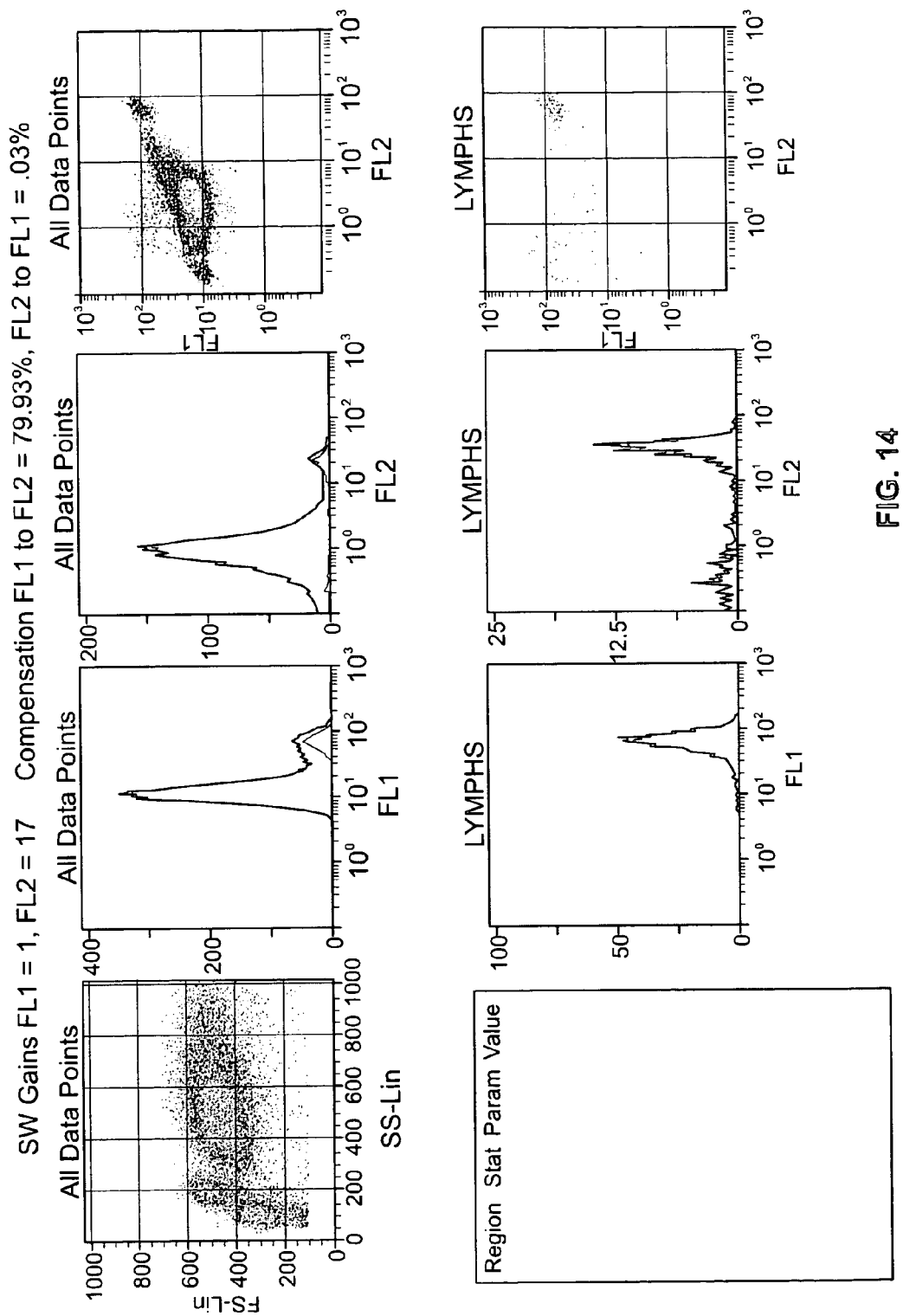
Figure 15:
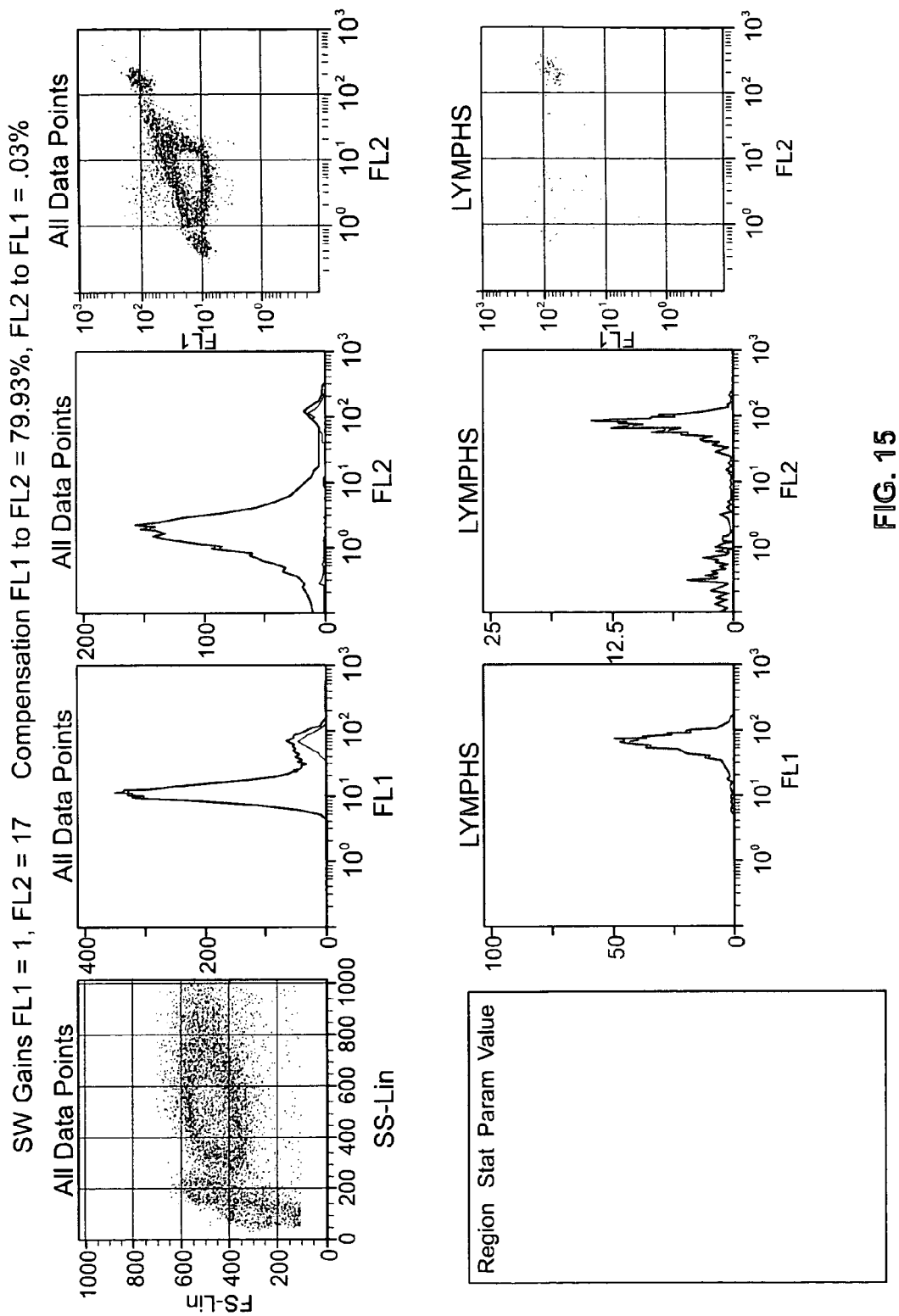

As shown in FIG. 3, the present cytometry system can apply a gain using a mathematical operator (which may be referred to, without limitation, as a software gain) to certain flow cytometry data. Such a gain may allow a shift of the display of the data in any of a number of desired manners, which still maintains the existing relationship between the points. For example, 10 consecutive data points one channel apart, beginning at channel 10 would have a range from 10 to 20. When these data points are adjusted by a software gain by applying a mathematical operator such as a multiplier of 1.5, the new range would be from 15 to 30, to maintain the relation between the points. Applying a mathematical operator (or software gain) allows the cytometry data to be presented in alternate locations on a display device without the need to adjust the flow cytometer's instruments' hardware settings. Generally, the mathematical operator applied will be multiplication or division, however, other variations, functions and operators may also be applied to achieve the same results, e.g., logarithmic functions, exponential functions, etc.

FIG. 3 also shows an example of data collected with a single hardware setting but displayed without loss of resolution at three different software gains: 1, 10 and 100. It is contemplated however that the invention can be used with a flow cytometer that has more data channels than display channels. It is also understood that this invention can also be used in connection with a cytometer that has any number of data channels.

As shown in FIGS. 4-15, the system may also adjust the compensation matrix to create the same crosstalk values when adjusting a software gain. Compensation is the process by which the fluorescence spillover originating from a fluorochrome other than the one specified for a particular PMT detector is subtracted as a percentage of the signal from other PMTs. For example, imagine that two fluorochromes "A" and "B," whose emission profiles are close together, are being detected in FL-1 and FL-2 channels respectively. Because the emission profiles are so close together, a portion of fluorochrome A spills over into FL-2 and conversely, some of fluorochrome B reaches FL-1. To calculate how much compensation needs to be applied to the dataset if both dyes are used simultaneously, some control readings are taken. Fluorochrome A would be run through the flow cytometer by itself and the percentage of its total emission that is detectable in FL-2 (spillover) is determined. The procedure would be repeated with fluorochrome B, except that this time FL-1 is spillover. When the present system applies a software gain, the compensation matrix may be adjusted to maintain the same relative crosstalk values without the need to recreate the compensation matrix and/or rerun the control samples.

For example, an embodiment of this invention can be applied to a two color compensation where a subtractive compensation amount of 10% is applied to FL2 (Fluorescent channel 2) from FL1 (Fluorescent channel 1), and a subtractive compensation amount of 0% is applied from FL2 to FL1. Accordingly, if FL1 had a value of 10 and FL2 had a value of 5 before compensation, then after compensation FL1 would have a value of 10, and FL2 a value of 4:

$$FL2Comp=FL2-(FL1*1)$$

$$FL1Comp=FL1-(FL2*0).$$

If a software gain using a mathematical operator, such as a multiplier of 2, is applied to FL1 only, then FL1 has a value 20 before compensation, and FL2 has a value of 5 before compensation. To keep the crosstalk the same from FL1 to FL2, then the 10% subtractive amount applied from FL1 to FL2 may be adjusted by the software gain applied to FL1. Therefore the new subtractive amount is 10% divided by the software gain of 2 or 5%. By applying a software gain of 2, this system and method may adjust the compensation mathematically to maintain the crosstalk values. FIGS. 4-15 graphically depict adjusting the data points of a cell sample by applying several different software gains and mathematically adjusting the compensation values to maintain the crosstalk values of the fluorescence signals of two different fluorophores. It is contemplated that that this invention can be used in connection with an infinite number of fluorophores.

In FIGS. 4-9, different software gains have been applied by the processor to FL1, but FL2 has no software gain applied. In FIGS. 10-15, different software gains have been applied by the processor to FL2, but FL1 has a fixed software gain applied. In each of FIGS. 4-15, density plots and line graphs are shown for the same set of data, but with the different software gains applied and shown on the displays.

The present system and method allows the compensation matrix to be corrected after and during data collection, as well as adjusting the data compensation matrix before collecting the data.

A software gain may also be used to adjust for day to day variability in cytometer intensities. When running a particle of a fixed intensity, a software gain can be applied and adjusted daily to remove variability in channel intensity without adjusting the cytometer's instruments' hardware.

Another example of applying a software gain to adjust for day to day variability in cytometer intensities is provided: A sample of particles with a known intensity are run on three consecutive days where the peak channel of the sample was observed to be 100, 80 and 125 respectively. A software gain, as represented below, is then applied to eliminate the flow cytometer instrumentation variability or drift:

Day 1 Channel=100, Adjustment Gain=1, Channel after software gain applied=100

Day 2 Channel=80, Adjustment Gain=1.25, Channel after software gain applied=100

Day 3 Channel=125, Adjustment Gain=0.8, Channel after software gain applied=100.

Figure 16:
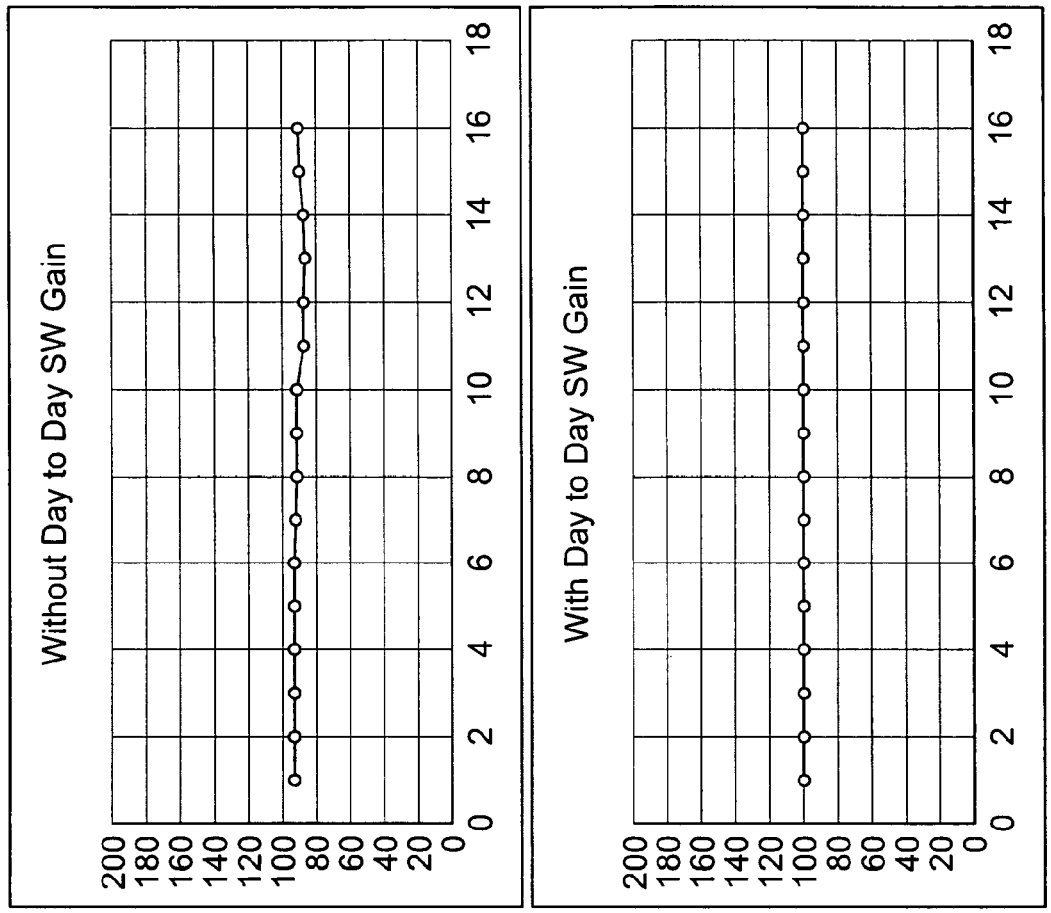
FIG. 16 shows a data table and charts of 16 exemplary cytometer runs with and without the software gain applied.

Another example of applying the software gain is shown in FIG. 16. A data table shows data from 16 different runs, including the run number, the mean channel number without a software gain applied for each run, the amount of the software gain applied and the standardized or mean channel number achieved by applying the software gain. A chart plotting the mean channel number without a software gain for each run is shown, as well as a chart plotting of the mean channel number with the software gain applied for each run is shown.

In still another embodiment, the invention uses a software gain to calibrate or standardize a cytometer to a standard intensity. By applying the software gain method/system of the present invention, a particle of know intensity can be used to standardize the parameters and adjusting the cytometer to the displayed intensity of the particle. In this embodiment, the software gain is split into two components. The first being the standardization or calibration component (component Y), the second being the user selected data channel for the location of the standard intensity (component Z) and may be the location at which the channel is displayed.

For example:

Bead B1 is known to have a standard intensity of 1.

Bead B2 is known to have a standard intensity of 2.

If Bead B1 was run on the cytometer, and it appeared in channel 10 for FL1, then a software gain Y of $\frac{1}{10}$ would standardize the FL1 channel to the intensity. If Bead B2 was run on the cytometer, and it appeared in channel 20 for FL1, then a software gain Y of $\frac{1}{10}$ would standardize the FL1 channel to the intensity. After such standardization Component Z would be the channel number that represents a standard intensity. This calibration or standardization could then be extended to all cytometers with this capability and thereby standardize all the instruments so that the results from one instrument would be the same as any other instrument which was standardized by this process.

In other words, a software gain can be used to standardize two products of known intensities. For example, if a cytometer is calibrated or standardized to a first bead of a known intensity, an assay of a second bead can be run, and the assay values from the second bead can be used to re-standardize the cytometer to the first bead of known intensity.

Process descriptions or blocks in figures should be understood as representing modules, segments, or portions of code which include one or more executable instruction for implementing specific logical functions or steps in the process. Alternate implementations are included within the scope of the embodiments of the present invention in which functions may be executed out of order from that shown or discussed, including substantially concurrently or in reverse order, depending on the functionality involved, as would be understood by those having ordinary skill in the art.

The method of the present invention may be implemented by a computer or computer system, such as one illustrated in FIG. 1. In addition, some or all of the implementation could take place in other hardware or software, which may or may not be part of the cytometer, such as signal processors or micro-controllers which provide information to the computer. It should be noted that the software can be stored on any computer readable medium for use by or in connection with any computer related system or method. In the context of this document, a "computer-readable medium" can be any medium that can store, communicate, propagate, or transport the program for use by or in connection with the instruction execution system, apparatus, or device. The computer readable medium can be for example, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). The software can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In another embodiment, where the system is implemented in hardware, the system can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Although the invention has been described with reference to the examples provided above, it should be understood that various modification can be made without departing from the spirit of the invention.

What is claimed is:

1. A flow cytometer system for analyzing the content of a sample and applying a software gain to standardize acquired data, the system comprising:
    a detector for measuring a first data signal associated with a control sample and a second data signal associated with a test sample; and,
    a processor for applying a pre-selected software gain to one or more data points corresponding to the second data signal to standardize the one or more data points while a hardware gain remains fixed,
    wherein the pre-selected software gain is based on the first data signal associated with a control sample having a known standard intensity.

2. The flow cytometer of claim 1 further comprising an analog to digital converter configured to convert the data signals into a digital data signals.

3. The flow cytometer of claim 1, further including a display.

4. The flow cytometer of claim 1, wherein the processor further applies a software gain to the one or more standardized data points, thereby enabling the one or more standardized data points to be presented on an alternative location on a display area while the hardware gain remains fixed.

5. A method for applying a software gain to standardize a flow cytometer, comprising the steps of:
    measuring, at a detector of a flow cytometer, measurements corresponding to a control sample having a known standard intensity, wherein the measurements include a detected intensity of the control sample;
    calculating, at a processor, a pre-selected software gain based on the detected intensity and the known standard intensity of the control sample;
    measuring, at the detector of the flow cytometer, measurements corresponding to a test sample; and
    applying, at the processor, the pre-selected software gain to one or more data points of the measurements corresponding to the test sample, to standardize the one or more data points while a hardware gain remains fixed.

* * * * *